(12) United States Patent
Sutter et al.

(10) Patent No.: US 11,337,669 B2
(45) Date of Patent: May 24, 2022

(54) AUTOMATIC POSITIONING OF AN X-RAY SOURCE BY WAY OF SEGMENTATION

(71) Applicant: Siemens Healthcare GmbH, Erlangen (DE)

(72) Inventors: Sven-Martin Sutter, Herzogenaurach (DE); Daniel Lerch, Weilersbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 47 days.

(21) Appl. No.: 17/036,746

(22) Filed: Sep. 29, 2020

(65) Prior Publication Data
US 2021/0093284 A1 Apr. 1, 2021

(30) Foreign Application Priority Data

Sep. 30, 2019 (EP) ..................................... 19200519
Sep. 18, 2020 (EP) ..................................... 20196929

(51) Int. Cl.
*A61B 6/00* (2006.01)
*G01N 23/046* (2018.01)
*A61B 6/06* (2006.01)
*A61B 6/08* (2006.01)

(52) U.S. Cl.
CPC ................. *A61B 6/547* (2013.01); *A61B 6/06* (2013.01); *A61B 6/08* (2013.01); *A61B 6/4208* (2013.01); *A61B 6/5258* (2013.01)

(58) Field of Classification Search
CPC ... A61B 6/0492; A61B 6/4208; A61B 6/5258; A61B 6/06; A61B 6/08; A61B 6/584; A61B 6/04; A61B 5/0037; G01N 12/046; G01N 2223/30; G01N 2223/303
See application file for complete search history.

(56) References Cited

U.S. PATENT DOCUMENTS 10,835,199 B2 * 11/2020 Chtcheprov ......... G01N 23/046
2010/0239070 A1    9/2010 Mohr

FOREIGN PATENT DOCUMENTS

| DE | 102009013572 A1 | 9/2010 |
| DE | 102012215496 A1 | 3/2014 |
| DE | 102013219137 A1 | 3/2015 |

OTHER PUBLICATIONS

Extended European Search Report dated Feb. 22, 2021.

* cited by examiner

*Primary Examiner* — Don K Wong
(74) *Attorney, Agent, or Firm* — Harness, Dickey & Pierce, P.L.C.

(57) ABSTRACT

At least one example embodiment provides a method for automatic positioning of an X-ray source of a medical X-ray system with a mobile X-ray detector. The method includes determining an examination region of the examination object, acquiring a position and a location of the examination object and the examination region by way of an optical position determining system, localizing the examination region, ascertaining a field point of the central ray of the X-ray source and a collimator size of the X-ray source based on the localized examination region, and automatic positioning of the X-ray source based on the field point and the collimator size.

20 Claims, 5 Drawing Sheets

AUTOMATIC POSITIONING OF AN X-RAY SOURCE BY WAY OF SEGMENTATION

PRIORITY STATEMENT

The present application hereby claims priority under 35 U.S.C. § 119 to European patent application numbers EP19200519 filed Sep. 30, 2019 and EP20196929 filed Sep. 18, 2020, the entire contents of which are hereby incorporated herein by reference.

FIELD

Example embodiments generally relate to methods for automatic positioning of an X-ray source by way of segmentation.

BACKGROUND

For image recordings with a freely positionable X-ray detector, for example, in the patient bed for imaging the lung, it has conventionally been necessary for the operator, for setting or positioning the X-ray radiator or the X-ray source, to estimate the orientation of the central ray and the spatial location of the X-ray detector, in particular, by eye. In addition, a direct view of the patient and of the collimated light field is possible.

SUMMARY

However, the direct view may be only to a limited extent since the operator often stands laterally to the patient and/or to the X-ray source. Due to this estimation, inaccuracies are possible and can lead to a loss of image quality.

At least one example embodiment provides a method for automatic positioning of an X-ray source by way of segmentation, an X-ray system, a computer program product and a computer-readable medium, which enable a more accurate alignment of the X-ray source to the X-ray detector.

At least one example embodiment provides a method for automatic positioning of an X-ray source of a medical X-ray system with a mobile X-ray detector. The method includes determining an examination region of the examination object, acquiring a position and a location of the examination object and the examination region by way of an optical position determining system, localizing the examination region, ascertaining a field point of the central ray of the X-ray source and a collimator size of the X-ray source based on the localized examination region and automatic positioning of the X-ray source based on the field point and the collimator size.

At least another example embodiment provides an X-ray system for carrying out the method having an X-ray source with an optical position determining system and a mobile X-ray detector.

At least another example embodiment provides a non-transitory computer program product storing a computer program, directly loadable into a memory apparatus of a control apparatus of an X-ray system, including a program to cause the control apparatus to perform the method of claim 1 when the computer program is executed in the control apparatus of the X-ray system.

At least another example embodiment provides a non-transitory computer-readable medium storing program portions, configured to be read in and executed by a computer unit, to carry out the method of claim 1 when the program portions are executed by the X-ray system.

BRIEF DESCRIPTION OF THE DRAWINGS

Example embodiments will now be described in more detail, making reference to the drawings. In the drawings.

DETAILED DESCRIPTION

Figure 1:
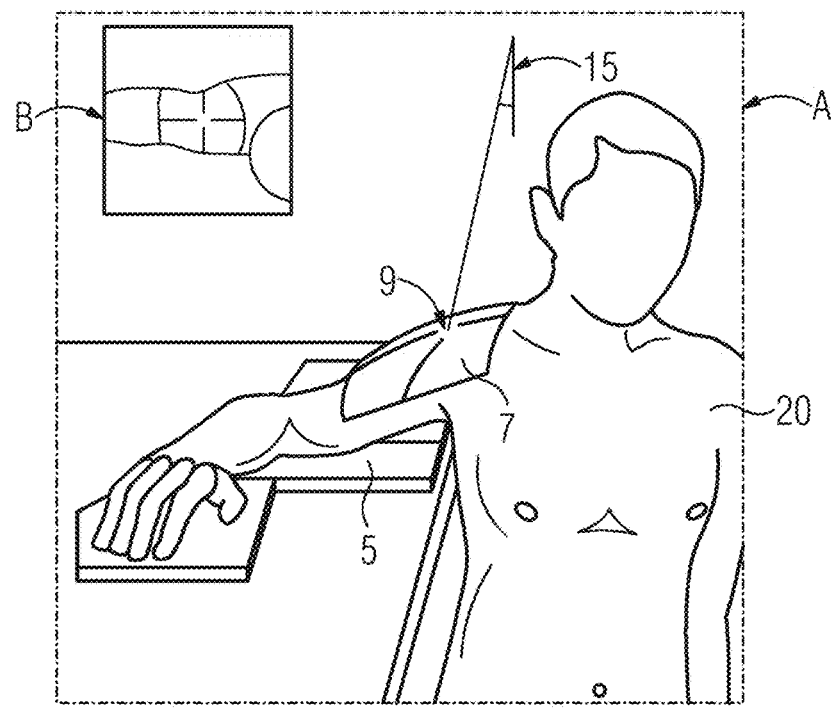
FIG. 1 is a schematic representation of a field point and a collimated examination region according to an example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable nonvolatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one example embodiment includes a method for automatic positioning of an X-ray source by way of segmentation, an X-ray system, a computer program product and a computer-readable medium as claimed.

At least one example embodiment relates to a method for automatic positioning of an X-ray source of a medical X-ray system with a mobile X-ray detector having the steps of determining, acquiring, localizing, ascertaining and of automatic positioning. In the step of determining, an examination region of the examination object is determined. In the step of acquiring, a position or positioning and location of the examination object and of the examination region is acquired by way of an optical position determining system. In the step of localizing, the examination region is localized. In the step of ascertaining, a field point of the central ray of the X-ray source and a collimator size of the X-ray source is ascertained based on the localized examination region. In the step of automatic positioning, the X-ray source is positioned based on the field point and the collimator size.

At least one example embodiment relates to use in conjunction with an X-ray system, in particular, a radiography system, with a mobile X-ray detector. The mobile X-ray detector can also be designated a freely positionable X-ray detector. The X-ray source can be, in particular, movable and/or adjustable. The X-ray source can be mounted on a movable carriage unit. The connection between the X-ray source and the carriage unit can be made, for example, by way of a bent arm with at least one joint. The X-ray source comprises a central ray. The X-ray source can emit an X-ray beam bundle which can be delimited by way of collimators. The size of the collimated X-ray beam bundle can be selected by way of the collimator size. The collimated X-ray beam bundle can then fall on the examination region during an X-ray recording. Ideally, the extent of the X-ray beam bundle on the incidence area of the examination object can substantially represent the extent of the examination area. Advantageously, the positioning of the X-ray source can be automated. Advantageously, an improved positioning can be achieved. Advantageously, an improved image quality can be achieved.

In the step of determining, the examination region of the examination object is determined, in particular, based on an examination type. In particular, the user can specify or input an examination type and/or an examination region. The input can take place, for example, by way of an input unit of the X-ray system. Alternatively, the X-ray source can be aligned in the direction of the examination region, at least roughly and the examination region can be "targeted". The examination region can be specified and or determined, in particular, by the user. The examination region can be designated the examination field.

In the step of acquiring, a position and a location of the examination object and the examination region are acquired by way of an optical position determining system. The step of acquiring can also be described with two steps, the first and the second acquisition. In the step of the first acquisition, a position and a location of an examination object can be acquired by way of an optical position determining system. The location can relate, in particular, to an arrangement in the room, for example, a position coordinate or a spatial coordinate. From the location, for example, a spacing of the X-ray source from the examination object or the examination region can be derived. The position can specify, for example, whether the patient is lying, sitting or standing. In particular, a position of the examination object can be acquired in relation to the use of positioning aids. The position can specify, for example, how the examination region is positioned or aligned relative to the X-ray source. The position can comprise the specification of a pose of the examination object. In the step of the second acquisition, the examination region can be acquired by way of the optical position determining system. The acquisition can comprise, in particular, a substantially three-dimensional recording of the examination object or of the examination region. The optical position determining system can be configured, in particular, as a 3D camera. The optical determining system can operate, in particular, in the visible or the invisible, in particular the infrared, region. In the step of localizing, the examination region is localized. The localizing can comprise, in particular, the position of the examination region and the extent of the examination region. The step of localizing can be based, in particular, on the acquisition of the examination region as a subregion of the examination object. In the step of ascertaining, a field point of the central ray of the X-ray source and a collimator size of the X-ray source are ascertained, in particular, based on the localized examination region. The field point can denote an incidence point of the central ray on the patient surface. In the step of automatic positioning, the X-ray source is positioned based on the field point and the collimator size. The X-ray source can thus advantageously be aligned as ideally as possible to the examination region and/or the X-ray detector. Subsequently, an X-ray recording of the examination region can be made.

In the X-ray order or the examination request or the examination type, the body part to be X-rayed or examined or the examination region is named. Based on the named body part, a pre-loaded organ program can be accessed.

With the aid of a camera mounted on the X-ray source or an optical position determining system, images, in particular, RGB and depth images or image data are recorded or acquired. From these images, an avatar of the patient or examination object can be calculated. The avatar can also be designated a, in particular virtual, patient model. This avatar can be segmented according to the X-ray order or the examination type or the examination region. Image segmentation takes place in the step of localizing. Alternatively or additionally, an image segmentation can take place in the step of ascertaining. In the context of the image segmentation, an assignment of segments to body regions and thus also to the examination region can take place. From the spatial location of the segment, in particular, the segment of the examination region, the position of the incidence point of the central ray can be determined or ascertained. The size of the radiation field of the X-ray source, in particular, the collimator size, can also be determined or ascertained from the segmentation. Thereby, the spacing between the X-ray source and the object (SOD) is known from the measurements of the depth images or an evaluation of the depth information with regard to the examination region. The location of the X-ray detector can be determined or ascertained from the location of the examination object or the examination region. In order to check the angular position of the X-ray detector, an item of information from angle sensors which can be included by the X-ray detector, can be used. The X-ray source can be moved automatically into the correct position, so that the central ray is adjusted in relation to the X-ray detector in accordance with the specifications. It is thereby assumed that the operator has positioned the X-ray detector under the body part to be X-rayed or behind the examination region (see FIG. 8).

According to at least one example embodiment, included in the step of localizing are the steps of creating, of segmenting and of localizing. In the step of creating, a patient model of the examination object is created based on the acquisition of the examination object or the examination region by way of the optical position determining system. The acquisition can also be designated the recording. In the step of segmenting, the patient model can be segmented based on the determined examination region. In the step of localizing, the examination region can be localized in the patient model.

The patient model can comprise, in particular, the examination region. The patient model can comprise the entire examination object or a part of the examination object. The patient model can comprise, in particular, the region of the field of view of the position determining system. With the aid, in particular, of image data recorded with a 3D camera, an avatar of the patient or the examination object can be generated. Through the segmentation of the avatar, according to the stipulation from the X-ray order or according to the examination type, the location of the X-ray detector can be ascertained from an extrapolated contour of the examination object. Optionally, the location of the X-ray detector can be ascertained by way of the information from the angle encoders or sensors which are possibly comprised by the X-ray detector. The X-ray source can then be positioned automatically according to the location of the X-ray detector. The collimator can be automatically adjusted to the body part or examination region to be X-rayed.

In particular, a 3D camera can be mounted and/or arranged on the X-ray source as the optical position determining system. Ideally, the optical axis of the optical position determining system corresponds to the central ray. If the optical axis of the optical position determining system does not match the central ray, calibration measurements can be carried out in order to enable an exact location determination or an optimum position of the X-ray source. Advantageously, the workflow in the examination can be improved. Advantageously, an improved image quality can be enabled.

Advantageously, an avatar of the examination object can be used for determining the location of the X-ray detector.

According to at least one example embodiment, included in the step of localizing are the steps of creating and of localizing. In the step of creating, a patient model of the examination object or an image data set of the examination object can be created based on the acquisition of the examination object by way of the optical position determining system. In the step of localizing, the examination region can be localized by way of a trained evaluating method based on a machine learning method. The trained evaluating method can also be designated a trained algorithm.

Firstly, by way of the position determining system, in particular, the camera or plurality of cameras, the examination object is sought, for example in the examination room, or its position is determined, in particular, in the step of acquiring. The examination object can lie on the patient table or a patient bed, or can stand in front of a Bucky wall stand or can sit in a wheelchair or beside the patient table.

From the examination type or the examination program or the examination order and the examination data contained therein, the information concerning the body part or organ to be X-rayed, i.e. the examination region, can be extracted, in particular, in the step of determining. The body part or the body region can now be sought by way of a trained algorithm and its location can be determined. With this, the field point of the central ray on this body part or the organ or the examination region can be determined (see FIGS. 1 and 2). In addition, the collimator size can be determined. In a further embodiment, the examination region of the X-ray system can be found independently and "approached" so that the examination region is included in the field of view of the optical position determining system. In addition, by way of the optical position determining system, the spacing between the X-ray source and the X-ray detector, the so-called SID, and the thickness of the examination object can be determined.

Machine learning in the sense of example embodiments comprises a computer-implemented technology in which an algorithm based upon existing data recognizes patterns and/or regularities and, using the same in relation to unknown new data, independently derives solutions. A precondition for finding an independent solution is a training phase in which an algorithm of machine learning is applied to a known, defined and usually very large data inventory in order to find the rules or predictions which aim toward a desired output or a desired result. The training can be configured as supervised or unsupervised training, wherein in the first variant, value pairs in the form of input values and correct output values belonging thereto are presented to the algorithm, whereas in the second variant, the algorithm must adapt itself independently based on the input values such that it supplies the correct output values.

Particularly advantageously, the algorithm of machine learning is configured as an artificial neural network. An artificial neural network is oriented toward the structure of a biological neural network such as, for example, a human brain. An artificial neural network preferably comprises, between an input layer and an output layer, a plurality of further layers, each comprising at least one node. Each node thereby corresponds to a processing unit, analogous to a biological neuron. Nodes within a layer of the network can be connected via directed connections (edges) to nodes of other layers. The connections define the data flow within the network. Each node therefore represents an operation which is applied to the input data. Furthermore, each node or each of its connections has a weighting parameter. By way of this weighting parameter, the influence or the importance of the output of a node as the input value for a receiving node is defined. In the training phase, which is preferably configured as supervised learning, the artificial neural network "learns", based on the training data, the weighting parameters for all the nodes or connections and adapts these until the output layer of the network supplies the correct output values.

According to at least one example embodiment, the procedure is further based upon the discovery that a trained algorithm of machine learning creates, in the context of its training, a firm connection between input values, here in the form of positions or coordinates and properties of the examination object or avatar, the examination type or similar, and output values, for example, in the form of the field point and the collimator size.

Particularly preferably, the step of localizing can be carried out by way of an algorithm. In a step for finding the examination object or the examination region per se, a trained algorithm can be used. Particularly suitable for this are algorithms of so-called deep learning, for example, in the form of "convolutional neural networks". In other words, according to this embodiment, by way of an algorithm of machine learning, a feature extraction is initially carried out and subsequently, a so-called classification, wherein the identified features are assigned to a position or location of the examination object or similar. As an alternative to a convolutional neural network, long short-term memory (LSTM) networks or recurrent neural networks (RNN) can be used which, in contrast to the aforementioned, have backward-directed feedback loops within the hidden network layers.

According to at least one example embodiment, a subsequently described artificial neural network can be used. The neural network responds to input values to a plurality of input nodes which are used to generate one or a plurality of outputs. In this exemplary embodiment, the neural network learns by adapting the weighting factors of the individual nodes based on the training data. Possible input values of the input nodes can be, for example, determined positions or properties as annotations of previous outputs that have previously been extracted from existing data sets. Alternatively, the neural network can be configured also to carry out the feature extraction. Any other desired input values can be made use of. The neural network weights the input values based on the learning process. The output values of the neural network preferably correspond to an ascertained field point, a collimator size and/or a position of the X-ray source. The output can take place via a single or a plurality of output nodes.

The artificial neural network preferably comprises a hidden layer which comprises a plurality of nodes. A plurality of hidden layers can be provided, wherein a hidden layer uses output values of another hidden layer as input values. The nodes of a hidden layer perform mathematical operations. An output value of a node hj thereby corresponds to a non-linear function f of its input values xi and the weighting factors wi. Following the receipt of input values xi a node hj carries out a summation of a multiplication of each input value xi weighted with the weighting factors wi, as defined by the following function:

$$h_j = f(\Sigma_i x_i \cdot w_{ij})$$

In particular, an output value of a node hj is formed as a function f of a node activation, for example, a sigmoidal function or a linear ramp function. The output values hj are transferred to the output node(s) oj. A renewed summation of a weighted multiplication of each output value hj as a function of the node activation f is calculated:

$$o_j = f(\Sigma_i h_i \cdot w'_{ij})$$

The neural network can be a feedforward neural network in which all the nodes process the output values of a previous layer in the form of its weighted sum as input values. Self-evidently, according to at least one example embodiment, other neural network types can be used, for example, feedback networks in which an input value of a node hj can simultaneously also be its output value.

By way of a method of supervised learning, the neural network can be trained to recognize patterns. A known procedure is back-propagation which can be applied for example embodiments. During the training, the neural network is applied to training input values and must generate corresponding, previously known output values. Mean square errors (MSE) between calculated and expected output values are calculated iteratively and expected output values are calculated and individual weighting factors are adjusted until the deviation between the calculated and expected output values lies below a pre-determined threshold.

Thereby, the orientation of the central ray and with the aid of the (specified) spacing between the X-ray source and the examination region or object and based on a deep learning-based training, the position of the X-ray source relative to the body part or organ or the examination region can be stipulated. Furthermore, a so-called skeletal tracking can be used as a trained evaluating method.

The central ray can now be aligned to the field point and positioned at the correct or optimum angle in the room, for example, in FIG. 1, 15 degrees, or to the orientation or location of the patient. The collimator can be adjusted to the correct or optimum size.

According to at least one example embodiment, a location of the X-ray detector is ascertained based on the location of the examination object, the patient model or the localized examination field.

In a subsequent step, the exact location of the X-ray detector can be sought or determined. The X-ray detector is expected in the "target region" of the central ray. Any angle sensors of the X-ray detector can provide or ascertain the orientation of a first plane in the room in which the X-ray detector is also located. The location of the first plane can be compared with a second plane which is given by a plane fitted or approached to the "rear side" of the avatar or the side thereof facing toward the X-ray detector. The angular position of the X-ray detector should substantially correspond to the orientation specified by the central ray and the angles defined by the respective examination or examination type.

In order to find the X-ray detector or for location determination of the X-ray detector, for example, optical methods can be used. For example, simple patterns in the visible light can be used. Alternatively or additionally, locating methods based on ultrasound or radar or electromagnetic locating methods for location determination of the X-ray detector can be used.

According to at least one example embodiment, the location of the X-ray detector is ascertained by way of angle sensors of the X-ray detector. The location of the X-ray detector can possibly be better ascertained in addition to other methods, for example, optical methods by way of angle sensors or other sensors. Alternatively or additionally, optical markers, for example, for using with infrared light can be used for position determination of the X-ray detector.

In one embodiment, a combination of locating methods can also be used, for example, the X-ray detector can initially be found optically and/or its location can be ascertained. If the X-ray detector is subsequently moved and is then possibly displaced completely behind the patient and/or the examination field, this position and/or location change can be ascertained with the aid of additionally installed sensors, for example, acceleration sensors. The thereby ascertained location of the X-ray detector can be compared with the assumed location in order, where relevant, to optimize the alignment of the X-ray detector to the central ray.

According to at least one example embodiment, the localized examination field is displayed on a display unit or by way of a light field projected onto the examination object.

As soon as the substantially exact location of the X-ray detector in the room as known, it can be shown whether the collimated region of the X-ray beam bundle is mapped entirely on the active region of the X-ray detector. Preferably (only) the mapping region impinging upon the active region can be marked and displayed in a virtual light field, for example, on a screen or a touch user interface or by way of a projected light field (see FIGS. 3 to 5). In addition or alternatively, the region which cannot be mapped on the active region of the X-ray detector can be emphasized.

According to at least one example embodiment, a proposal for positional correction of the examination object is output.

In a further embodiment, after the positioning of the patient or the examination object, in particular, with determined recordings or examination types, additionally or alternatively, the intended position of the patient and/or of the examination object and/or of the examination region can be checked. For example, the angle between the shoulder axis and the X-ray detector can be measured with the aid of the 3D information, displayed and compared with a target value, a so-called textbook value (see FIGS. 6 and 7). A target-versus-actual representation can be displayed. An adjustment to the optimum alignment of the examination object can be carried out. Furthermore, an operator guidance for patient positioning can be provided, in particular, guided virtually or by way of projections.

The examination workflow can advantageously be largely retained. The examination workflow can advantageously be supported step-wise in the individual phases of the examination or recording.

The position of the X-ray source can be focused on the region to be X-rayed and/or the examination region rather than on the middle of the X-ray detector. Advantageously, the collimation of the X-ray beam bundle can be optimized. Advantageously, the patient dose can be reduced. Advantageously, an optimization of the patient position can be enabled.

Based on the assumption that the X-ray detector can be expected in a substantially known region, the demands placed on the X-ray detector locating system can be reduced, at least for the distance range. Advantageously, the system can be configured inexpensively.

According to at least one example embodiment, a movement of the examination object is acquired by way of the optical position determining system. Once the movement has ceased, the positioning of the X-ray source can be corrected in that the field point and the direction vector of the X-ray source are calculated anew and adjusted or set. In one embodiment, the field point and the collimator size can be determined iteratively, in particular, under the influence of patient movements. By way of the field point and, where relevant, by way of an angle specified or pre-determined by the examination type or the examination region, the central ray of the X-ray source can be aligned along the direction vector. The acquisition of the movement can be used in a further embodiment for a breathing trigger wherein a plurality of breathing cycles are acquired and evaluated so that the X-ray recording can be made in a resting phase or a low-movement phase in a subsequent breathing cycle based on the evaluated breathing cycles. For example, for lung recordings, the X-ray irradiation is typically triggered, and the X-ray recording is carried out, at maximum inspiration. Advantageously, the image quality can be improved.

According to at least one example embodiment, a renewed acquisition and a renewed localization of the examination region is carried out and the positioning of the X-ray source is corrected based on the renewed localization.

In a further embodiment, small movements of the examination object, for example, jerks, gasps or coughs can be corrected after cessation of the movement, wherein the field point and, if relevant, therefrom the direction vector of the X-ray source can be recalculated and adjusted. Subsequently, a display can take place in order to inform the operator about the correction. Advantageously, a correction can be carried out after a patient movement, so that the image quality can be improved.

According to at least one example embodiment, the central ray of the X-ray source is aligned at pre-determined angle to the examination region, based on the examination region or an examination type. Dependent upon the examination type or examination region, an angle of the central ray to the examination region can be pre-determined. This angle can be taken into account in the ascertainment of the field point and the subsequent automatic positioning.

According to at least one example embodiment, the central ray of the X-ray source is aligned substantially perpendicular to the X-ray detector. The, in particular typical, alignment of the central ray can be formed along the surface normal of the X-ray detector. Advantageously, a good image quality can be achieved.

According to at least one example embodiment, the central ray of the X-ray source deviates from an alignment substantially perpendicular to the X-ray detector and an image correction of an X-ray recording is carried out in respect of the deviation. If the central ray deviates from the surface normal of the X-ray detector, an image correction can be carried out in order advantageously to improve the image quality.

In a further embodiment, the two requirements, specifically that the X-ray source is aligned at an optimum angle to the (free) X-ray detector, that is, it is usually aligned perpendicularly, and that the X-ray source is at an optimum angle to the anatomical structure or to the examination region, can be considered. The optimum angle to the anatomical structure can be significant, in particular, during orthopedic examinations, for example, of joint cavities. The two requirements cannot be well fulfilled simultaneously in every case, for example, because the patient is positioned on the patient bed or a cushion in a way that is unsuitable therefor. For example, the (free) X-ray detector cannot be arranged in such a way that the X-ray source is aligned optimally or ideally relative to the anatomical structure and simultaneously to the X-ray detector. In these cases, at least if no grid is used on the X-ray detector, the X-ray source can preferably be aligned optimally to the anatomical structure. Advantageously, the alignment of the X-ray source to the examination region can be determined reliably even if the X-ray detector is not visible behind the examination object.

A possibly inaccurate alignment in relation to the X-ray detector, which can become visible in the form of a distortion of the recording, can subsequently be corrected digitally. The correction can take place based on the position parameters of the X-ray source as set, specifically the location and angle, and those of the X-ray detector, based on measurements of location sensors or gyrosensors. The location of the anatomical structure can be determined by the optical position determining system, for example, a 3D camera. The angular deviation of the body part and/or the examination region can be calculated therefrom. The deviation can be used for correction or distortion correction of the two-dimensional (X-ray) recording.

At least one example embodiment further relates to an X-ray system configured to carry out a method according to another example embodiment. The X-ray system can be, in particular, a (mobile) radiography system. The X-ray system has an X-ray source with an optical position determining system and a mobile X-ray detector. The optical axis of the position determining system can ideally correspond to the central ray of the X-ray source. Otherwise, a deviation from the central ray can be taken into account during the ascertainment.

At least one example embodiment further relates to a computer program product with a computer program which can be loaded directly into a memory apparatus of a control apparatus of an X-ray system, having program portions in order to carry out all the steps of a method according to another example embodiment when the computer program is executed in the control apparatus of the X-ray system.

At least one example embodiment further relates to a computer-readable medium on which program portions that are configured to be read in and executed by a computer unit are stored, in order to carry out all the steps of a method according to another example embodiment when the program portions are executed by the X-ray system.

FIG. 1 shows a field point 9 a and a collimated examination region 7 according to an example embodiment. Firstly, a side view A is shown. The examination object 20 is seated beside a table and the arm with the examination region 7 is supported on the table by way of a positioning aid. The X-ray detector 5 is positioned under the examination region 7 on the table. The examination region 7 lies in the area of the shoulder. An angle 15 is specified between the room vertical and the central ray, this being, for example, 15 degrees. In addition, the region collimated by way of the collimator size as set is represented as the examination region 7 and the field point 9. In the plan view B, the examination region is also shown. The plan view B can be displayed, for example, by a display unit. The plan view B can be, in particular, a plan view with a view along the optical axis or the central ray.

Figure 2:
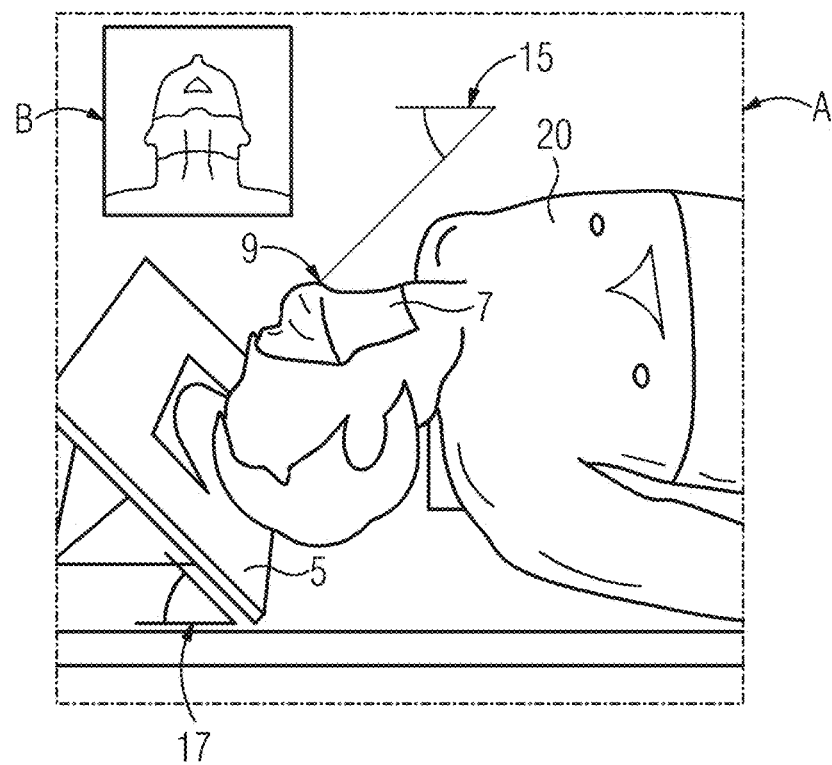
FIG. 2 is a schematic representation of a field point ascertained and a collimated examination region according to an example embodiment.

FIG. 2 shows a field point 9 and a collimated examination region 7 according to an example embodiment. Firstly, a side view A is shown. The examination object 20 lies on its back with a hyperextended head. The examination region 7 is situated in the area of the face. The X-ray detector 5 is positioned by way of a positioning aid on the table at an angle 17 to the table surface. An angle 15 is specified between the room horizontal and the central ray, this being, for example, 45 degrees. In addition, the region collimated by way of the collimator size as set is represented as the examination region 7 and the field point 9. In the plan view B, the examination region is also shown. The plan view B can be displayed, for example, by a display unit.

Figure 3:
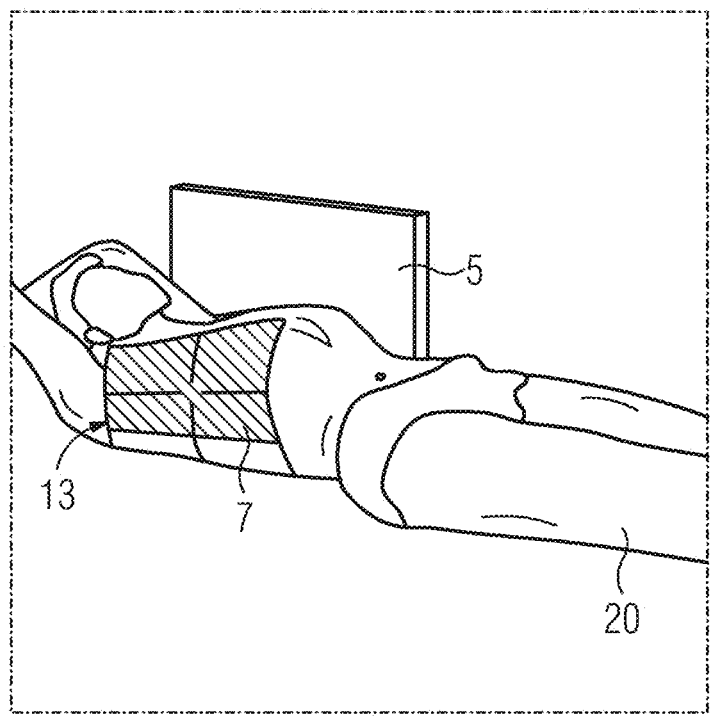
FIG. 3 is a schematic representation of a display of the collimated examination field relative to the examination object and the X-ray detector according to an example embodiment.

FIG. 3 shows an exemplary configuration of a display of the collimated examination field 7 relative to the examination object 20 and the X-ray detector 5 in a first embodiment. The display can take place, for example, by way of a, possibly virtual, light field 13. The light field 13 can be projected onto the examination object 20. Alternatively, a virtual light field 13 can be overlaid onto a camera image on a display unit. As soon as the substantially exact location of the X-ray detector 5 in the room is known, it can be shown whether the collimated region of the X-ray beam bundle is mapped entirely on the active region of the X-ray detector. Preferably only the mapping region impinging upon the active region can be marked and displayed in a virtual light field 13, for example, on a screen or a touch user interface or by way of a projected light field. The collimated region of the examination field 7 which is mapped on the active region of the X-ray detector is shown.

Figure 4:
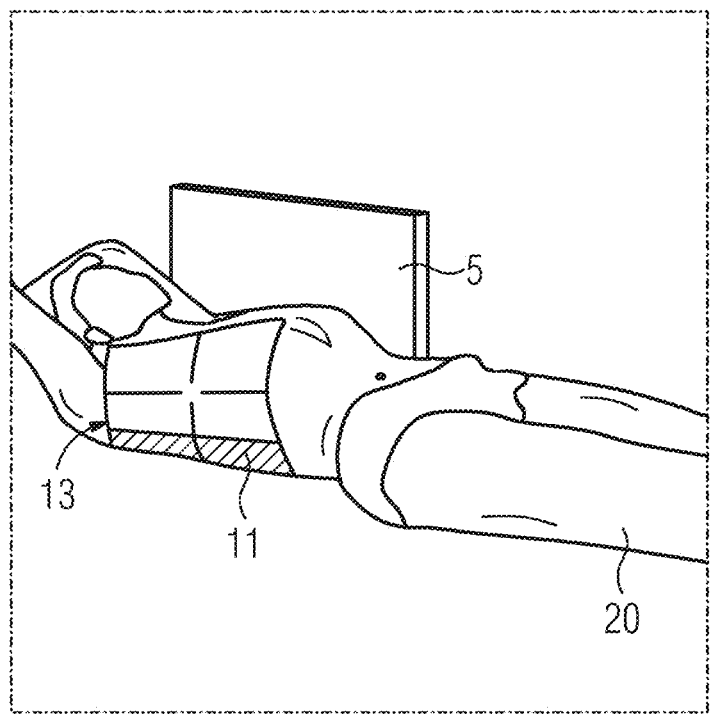
FIG. 4 is a schematic representation of a display of the collimated examination field relative to the examination object and the X-ray detector in a second embodiment.

FIG. 4 shows an exemplary embodiment of a display of the collimated examination field 7 relative to the examination object 20 and the X-ray detector 5 in a second embodiment. The region 11 is shown which is situated outside the active region of the X-ray detector.

Figure 5:
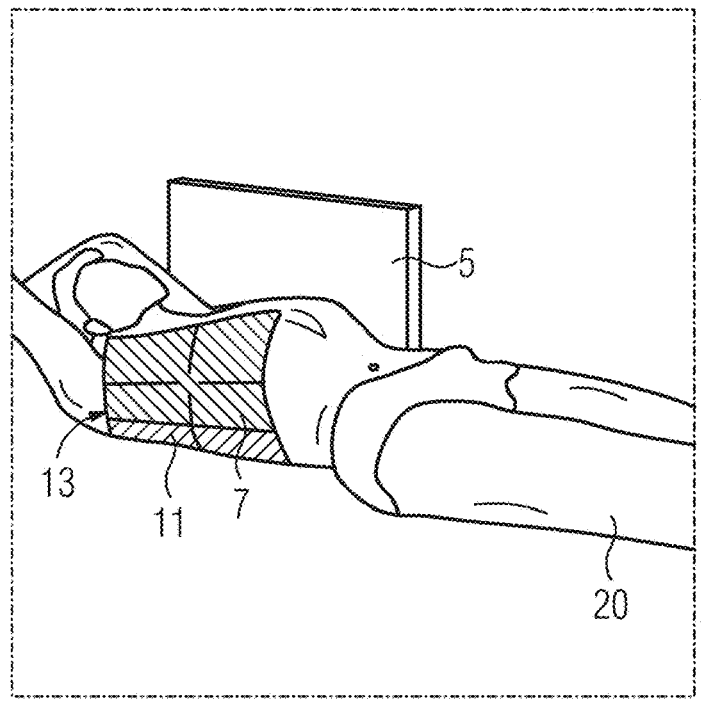
FIG. 5 is a schematic representation of a display of the collimated examination field relative to the examination object and the X-ray detector according to an example embodiment.

FIG. 5 shows an exemplary representation of a display of the collimated examination field 7 relative to the examination object 20 and the X-ray detector 5 in a third embodiment. Both the collimated region of the examination field 7 which is mapped on the active region of the X-ray detector is mapped, and also the region 11 which is situated outside the active region of the X-ray detector is shown. The regions 7 and 11 are shown distinguishably, for example, by way of different colors.

Figure 6:
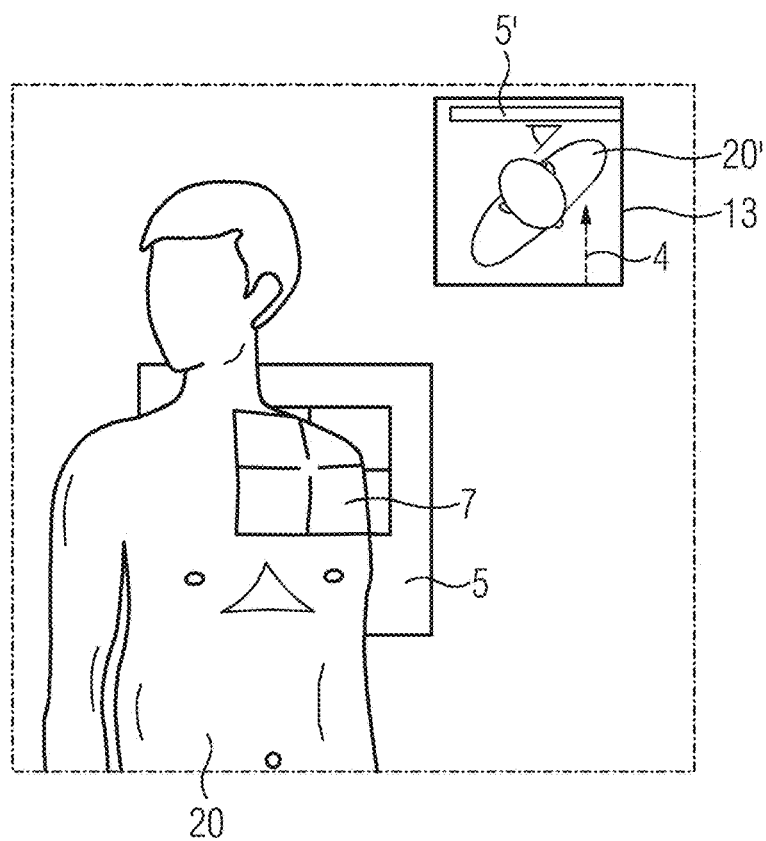
FIG. 6 is a schematic representation of a checking according to an example embodiment of a location or position of the examination object according to an example embodiment.

FIG. 6 shows an exemplary embodiment of the checking of a location or position of the examination object 20 in a first embodiment. After the positioning of the examination object, in particular, with specific recordings or examination types, the intended location or position of the examination object and/or of the examination region is checked. The examination object 20 is positioned standing at an angle in front of the X-ray detector 5. The examination field 7 is collimated. In a plan view, a target position is shown, for example, on a display unit. The examination object 20' is to be positioned in a pre-determined angular range ideally in front of the X-ray detector 5'. The central ray 4 is also displayed.

Figure 7:
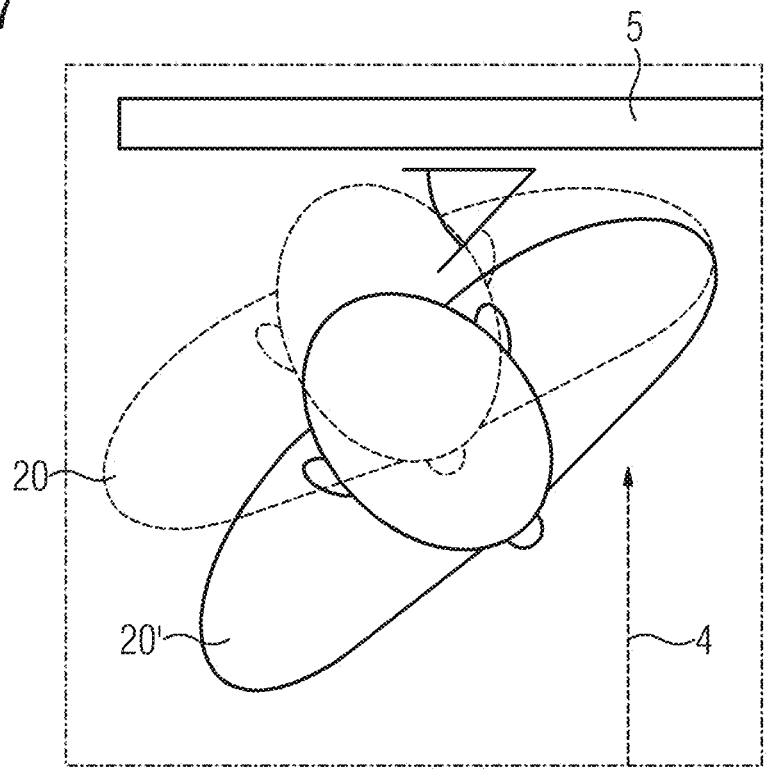
FIG. 7 is a schematic representation of a checking of a location or position of the examination object according to an example embodiment.

FIG. 7 shows an exemplary embodiment of the checking of a location or position of the examination object 20 in a second embodiment. A proposal for positional correction of the examination object 20 is output, for example, on a display unit. For example, the angle between the shoulder axis and the X-ray detector can be measured with the aid of the 3D information, displayed and compared with a target value, a so-called textbook value. A target-versus-actual representation is displayed. An adjustment to the optimum alignment of the examination object 20 can be carried out. Furthermore, an operator guidance for patient positioning can be provided, in particular, guided virtually or by way of projections. The target position of the model examination object 20' is possibly shown with an angle stipulation. The actual position of the examination object 20 is shown overlaid. A color coding of the representation of the examination object can display a correct (green) or incorrect (red) positioning or location of the examination object 20. In addition, the central ray 4 can be displayed for orientation.

Figure 8:
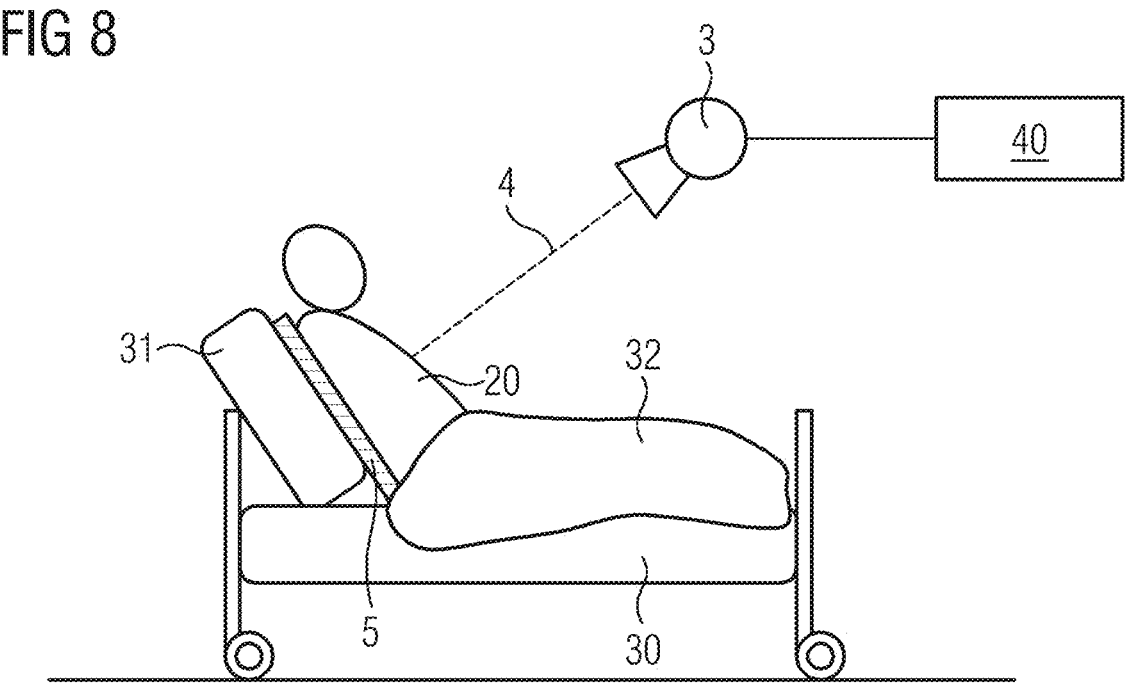
FIG. 8 is a schematic representation of an X-ray system according to an example embodiment.

FIG. 8 shows an X-ray system for carrying out a method according to at least one example embodiment. The X-ray system has an X-ray source 3 with an optical position determining system and a mobile X-ray detector 5. The examination object 20 is positioned, for example, in a patient bed 30 by way of cushions 31. The X-ray source 3 with the central ray 4 irradiates, for example, the trunk of the examination object 20. The X-ray detector 5 is situated, for example, behind the examination object 20 along the back. The X-ray detector 5 is arranged between the cushion 31 and the examination object 20. The examination object is covered with a blanket 32. The X-ray system further has a computer unit 40.

Figure 9:
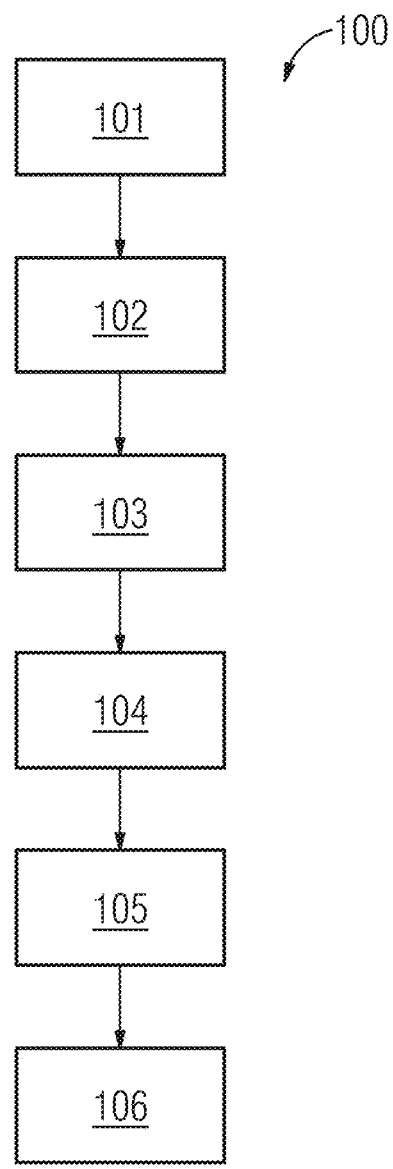
FIG. 9 is a schematic representation of a method according to an example embodiment.

FIG. 9 shows an example embodiment of the method 100. The method 100 for automatic positioning of an X-ray source 3 of a medical X-ray system with a mobile X-ray detector 5 has the steps of determining 101, acquiring 102, localizing 103, ascertaining 104 and of automatic positioning 105.

In the step of determining 101, an examination region of the examination object is determined. In the step of acquiring 102, a position and a location of the examination object and the examination region are acquired by way of an optical position determining system. In the step of localizing 103, the examination region is localized. In the step of ascertaining 104, a field point of the central ray of the X-ray source and a collimator size of the X-ray source are ascertained based on the localized examination region. In the step of automatic positioning 105, the X-ray source is positioned based on the field point and the collimator size. A further step of displaying 106 on a display unit can take place. Furthermore, the step of recording an X-ray recording with the positioned X-ray source can take place.

The step of localizing 103 can comprise the following steps: the step of creating a patient model of the examination object based on the acquisition of the examination object by way of the optical position determining system, the step of segmenting the patient model based on the determined examination region, and the step of localizing the examination region in the patient model.

In another embodiment, the step of localizing 103 can comprise the following steps: the step of creating a patient model of the examination object or an image data set of the examination object based on the acquisition of the examination object by way of the optical position determining system, and the step of localizing the examination region by way of a trained evaluating method based on a machine learning method. The image data set can be generated, in particular, by way of the optical position determining system. For evaluating the image data set, known image recognition methods can be used.

A location of the X-ray detector is ascertained based on the location of the examination object, the patient model or the localized examination field. The location of the X-ray detector can, if relevant, additionally be ascertained by way of angle sensors of the X-ray detector.

A movement of the examination object can be acquired by way of the optical position determining system. A renewed acquisition and a renewed localization of the examination region can be carried out and the positioning of the X-ray source can be corrected based on the renewed localization.

In the step of displaying 106, the localized examination field is displayed on a display unit or by way of a light field projected onto the examination object.

The central ray of the X-ray source is aligned at predetermined angle to the examination region, based on the examination region or an examination type. The central ray of the X-ray source can be aligned substantially perpendicular to the X-ray detector. Alternatively, the central ray of the X-ray source can deviate from an alignment substantially perpendicular to the X-ray detector and an image correction of an X-ray recording can be carried out in respect of the deviation. A proposal for positional correction of the examination object can be output, in particular, on the display unit.

Although example embodiments have been described in detail, the example embodiments are not restricted by the examples given and other variations can be derived therefrom by a person skilled in the art without departing from the protective scope of example embodiments.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic positioning of an X-ray source of a medical X-ray system with a mobile X-ray detector, the method comprising:
   determining an examination region of an examination object;
   acquiring a position and a location of the examination object and the examination region by way of an optical position determining system;
   localizing the examination region;
   ascertaining a field point of a central ray of the X-ray source and a collimator size of the X-ray source based on the localized examination region; and
   automatic positioning of the X-ray source based on the field point and the collimator size.

2. The method as claimed in claim 1, wherein the localizing includes:
   creating a patient model of the examination object based on the acquisition of the examination object by way of the optical position determining system,
   segmenting the patient model based on the determined examination region, and
   localizing the examination region in the patient model.

3. The method as claimed in claim 1, wherein the localizing includes:
   creating a patient model of the examination object or an image data set of the examination object based on the acquisition of the examination object by way of the optical position determining system, and
   localizing the examination region by way of a trained evaluating method based on a machine learning method.

4. The method as claimed in claim 1, wherein a location of the X-ray detector is ascertained based on the location of the examination object, a patient model or the localized examination region.

5. The method as claimed in claim 1, wherein the location of the X-ray detector is ascertained by way of angle sensors of the X-ray detector.

6. The method as claimed in claim 1, wherein a movement of the examination object is acquired by way of the optical position determining system.

7. The method as claimed in claim 6, wherein a renewed acquisition and a renewed localization of the examination region is carried out and the positioning of the X-ray source is corrected based on the renewed localization.

8. The method as claimed in claim 1, wherein the localized examination region is displayed on a display unit or by way of a light field projected onto the examination object.

9. The method as claimed in claim 1, wherein the central ray of the X-ray source is aligned at pre-determined angle to the examination region, based on the examination region or an examination type.

10. The method as claimed in claim 1, wherein the central ray of the X-ray source is aligned substantially perpendicular to the X-ray detector.

11. The method as claimed in claim 1, wherein the central ray of the X-ray source deviates from an alignment substantially perpendicular to the X-ray detector and an image correction of an X-ray recording is carried out in respect of the deviation.

12. The method as claimed in claim 1, wherein a proposal for position correction of the examination object is output.

13. An X-ray system for carrying out the method of claim 1, having:
 an X-ray source with an optical position determining system; and
 a mobile X-ray detector.

14. A non-transitory computer program product having a computer program, directly loadable into a memory apparatus of a control apparatus of an X-ray system, including program portions to cause the control apparatus to perform the method of claim 1 when the computer program is executed in the control apparatus of the X-ray system.

15. A non-transitory computer-readable medium storing program portions, configured to be read in and executed by a computer unit, to carry out the method of claim 1 when the program portions are executed by the X-ray system.

16. The method as claimed in claim 2, wherein a location of the X-ray detector is ascertained based on the location of the examination object, the patient model or the localized examination region.

17. The method as claimed in claim 2, wherein the location of the X-ray detector is ascertained by way of angle sensors of the X-ray detector.

18. The method as claimed in claim 2, wherein a movement of the examination object is acquired by way of the optical position determining system.

19. The method as claimed in claim 18, wherein a renewed acquisition and a renewed localization of the examination region is carried out and the positioning of the X-ray source is corrected based on the renewed localization.

20. The method as claimed in claim 2, wherein the localized examination region is displayed on a display unit or by way of a light field projected onto the examination object.

* * * * *